United States Patent [19]
Anderson et al.

[11] Patent Number: 5,398,695
[45] Date of Patent: Mar. 21, 1995

[54] CARDIOPULMONARY PERFORMANCE ANALYZER HAVING DYNAMIC TRANSIT TIME COMPENSATION

[75] Inventors: David M. Anderson, St. Paul; Shawn McCutcheon, White Bear Lake, both of Minn.

[73] Assignee: Medical Graphics Corporation, St. Paul, Minn.

[21] Appl. No.: 217,231

[22] Filed: Mar. 24, 1994

[51] Int. Cl.$^6$ ............................................. A61B 5/08
[52] U.S. Cl. ................................... 128/719; 128/725
[58] Field of Search ............ 128/716, 719, 725, 205.27

[56] References Cited

U.S. PATENT DOCUMENTS 4,368,740  1/1983  Binder ................................. 128/719
4,463,764  8/1984  Anderson et al. ................... 128/719
5,038,773  8/1991  Norlien et al. .

Primary Examiner—Lee S. Cohen
Assistant Examiner—Brian M. Grier
Attorney, Agent, or Firm—Haugen and Nikolai

[57] ABSTRACT

The gas sample line in a cardiopulmonary performance analyzing system is designed to include a flow sensor for measuring the rate of flow of the gas sample being drawn and is used to adjust the initial transit time value measured at the time of system calibration for a known value of flow in arriving at a new or current transit time value at the time that a test is actually being performed on a patient. This dynamically compensates the transit time for variations in the sample flow rate, thus providing a system with accuracy that is not dependent upon maintaining constant sample flow rates.

2 Claims, 1 Drawing Sheet

CARDIOPULMONARY PERFORMANCE ANALYZER HAVING DYNAMIC TRANSIT TIME COMPENSATION

BACKGROUND OF THE INVENTION

I. Field of the Invention

This invention relates generally to cardiopulmonary performance analyzing equipment, and more particularly to a method and apparatus for automatically and dynamically aligning respiratory flow measurements with the measurements of individual gas concentrations of $O_2$, $CO_2$, etc., in the respiratory gas mixture, irrespective of changes in flow rates in the system's sampling line.

II. Discussion of the Prior Art

In the Anderson et al. U.S. Pat. No. 4,463,764 there is described a cardiopulmonary performance analyzing system for real-time, breath-by-breath acquisition, analysis and display of an individual's cardiopulmonary related parameters. In this system, a mouthpiece member containing a pneumotach is coupled to a differential pressure transducer allowing inspiratory and expiratory flow measurements to be taken. Also coupled to the mouthpiece member is a sample line leading to one or more gas analyzers which are used to measure the percentage concentration of particular gases, such as $O_2$ and $CO_2$ contained in the sample being drawn through the sample tube by a vacuum pump or the like. Signals from the gas analyzers are then fed into a computer-based waveform analyzer along with the flow information from the pneumotach and differential pressure transducer. While not discussed in the Anderson et al. '764 patent, it is also common practice to include a particulate filter in the sample line.

The waveform analyzer in the Anderson et al. patent not only provides for the sampling of the various analog input parameters and converting them to digital signals but it also adjusts the phase shift of the dynamic signals pertaining to the individual gas concentrations so that they will be properly aligned, time-wise, so as to be correlated with the flow. Because proper phase alignment is dependent upon the transit time of the flow sample in the sample line and because the sample flow in the sample line does not always remain constant, it is somewhat difficult to maintain precise time-wise alignment between respiratory flow and the percentage concentration of respiratory gas waveforms over prolonged periods. For example, the system may be calibrated at the onset of a patient test, but in the course of the test the particulate filter in the sample line may be affected by moisture particles, causing a variation in the sample flow rate as it becomes loaded. Also, there can be variations in the pump of the vacuum pump used for drawing the sample through the sample line. Accordingly, a need exists for a cardiopulmonary performance analyzer that allows intra-test adjustment for variations in the transit time of gas samples in arriving at the phase delay between the outputs from the gas analyzers and the respiratory flow measurement at the particular sample time.

It is accordingly a principal object of the present invention to provide a method and apparatus for dynamically aligning measured respiratory flow with $O_2$ and $CO_2$ signals to compensate for changing sample line flow rates.

Another object of the invention is to provide a method and apparatus for precisely determining the phase delay between the time that a sample is introduced into the sample line and the time in which the several respiratory gas analyzers generate their outputs indicative of the percentage concentration of the particular gas in the sample

SUMMARY OF THE INVENTION

In accordance with the present invention there is provided a cardiopulmonary performance analyzer of the type having a sample line leading to at least one respiratory gas analyzer where that gas analyzer is adapted to measure the percentage concentration of a particular gas present in the sample line. A means, such as a vacuum pump, is also provided in the sample line for drawing a sample of respiratory gas through the sample line. Further in accordance with the present invention, the cardiopulmonary performance analyzer will include a flow meter for measuring the volume rate of flow of inspired and expired respiratory gases by the patient. The present invention adds to the above-described assembly apparatus for compensating for transit time delays between the time that a gas sample is drawn into the sample line and the time that the various gas analyzers included in the sample line produce their output response. The apparatus includes a microprocessor operative at an initial calibration time for computing and storing the transit time, $t_c$, of a gas sample drawn into the sample line to reach one of the gas analyzers for a known sample flow rate, $F_c$. A sample flow measuring means, such as a hot-wire anemometer, is provided in the sample line for producing a signal, $F_s$, that is proportional to the rate of flow of a gas sample through the sample line during the course of a cardiopulmonary test on a patient. The microprocessor is values of $t_c$ and $F_c$ and computing a present gas transit time, $t_p$, arranged to receive the signal, $F_s$, and the previously stored values of $t_c$ and $F_c$ and computing a present gas transit time, $t_p$, in accordance with the equation, $t_p = t_c (F_c/F_s)$. The computed value, $t_p$, is then added to the known, fixed response time of the gas analyzer in question in arriving at the total phase delay. The phase delay is then used to time-wise align the measured percentage concentration of the particular gas ($O_2$ or $CO_2$) with the measured volume rate of flow of the inspired and expired respiratory gases measured using the pneumotach and differential pressure sensor combination.

DESCRIPTION OF THE DRAWINGS

The foregoing features, objects and advantages of the invention will become apparent from the following detailed description of a preferred embodiment, especially when considered in conjunction with the accompanying drawings in which.

DESCRIPTION OF THE PREFERRED EMBODIMENT

Figure 1:
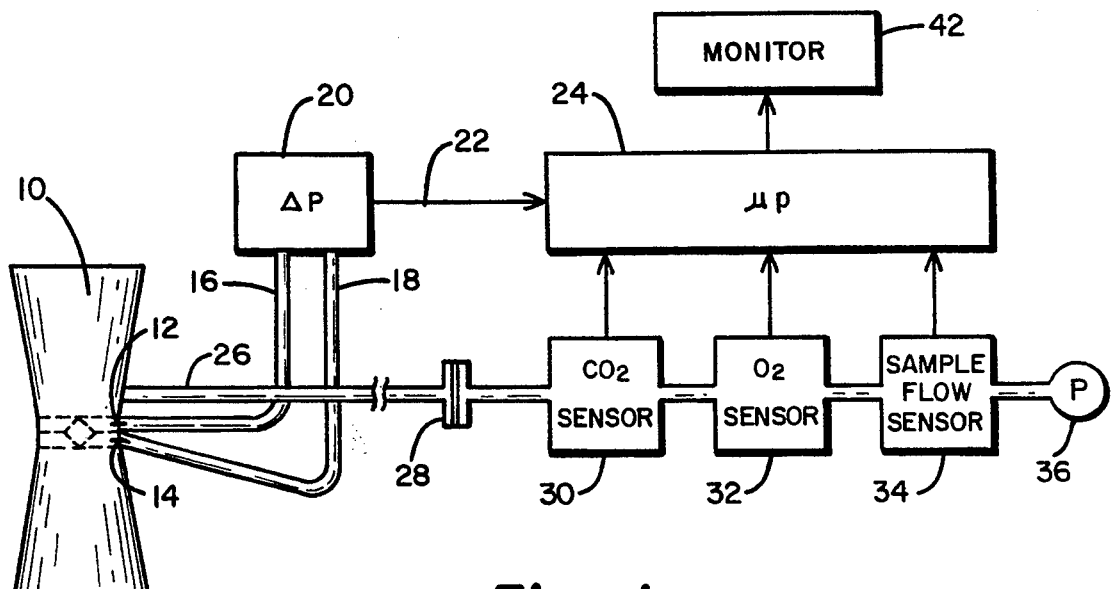
FIG. 1 is a schematic block diagram of the portion of a cardiopulmonary performance analyzer incorporating the present invention.

Referring first to FIG. 1, there is indicated generally by numeral 10 a pneumotach mouthpiece member which is placed in the patient's mouth and used to measure the volume rate of flow of both inspiratory and expiratory gases. With no limitation intended, the pneumotach mouthpiece 10 may be constructed in accordance with that disclosed in the Norlien et al. U.S. Pat. No. 5,038,773 which is assigned to the assignee of the present invention. The mouthpiece 10 has first and second pressure sensing ports 12 and 14 which are coupled by tubes 16 and 18 to a pair of inputs to a differential pressure transducer 20. The differential pressure transducer is operative to produce a voltage output on line 22 that is proportional to the difference in pressure at the ports 12 and 14. This voltage is then converted to a digital signal by an analog/digital converter (not shown) forming a part of the microprocessor module 24.

Also connected to the mouthpiece 10 by means of tubing 26 is a sampling line that includes a particulate filter 28, one or more gas analyzers 30, 32, a sample line flow sensor 34 and a vacuum pump 36. The vacuum pump 36 draws a gas sample through the tube 26 and through the carbon dioxide sensor 30 and the oxygen sensor 32.

Those skilled in the art appreciate that the $CO_2$ analyzer and the $O_2$ analyzer each have a known, fixed response time, $t_r$. The response time may, for example, comprise the amount of time required for the sensor to reach 50 percent of its maximum output. In addition to this fixed response time, the total phase delay between the drawing of the sample and the end of the response time for the sensor 30 or 32 also includes a variable factor relating to the transit time of the sample through the sample line to the particular sensor in question. The transit time is variable because the flow rate through the sample line can also vary. Variation in sample flow rate may be due to changes in the condition of the particulate filter 28 and/or variations introduced by the motor-driven vacuum pump 36.

In accordance with the present invention, there is provided in the sample line a sample flow sensor 34. With no limitation intended, this sample flow sensor may comprise a hot-wire anemometer. However, any other known device capable of measuring variations in gas flow rate in the order of magnitude existing in cardiopulmonary test apparatus may also be employed.

The sample gas sensors 30 and 32 as well as the sample flow sensors 34 each provides an analog output which is applied to the microprocessor 24. As with the flow measurement on line 22, these outputs are applied to a suitable analog/digital converter so that the microprocessor can operate on digital signals as operands in performing various computations defined by a program stored in the memory of the microprocessor. The output from the microprocessor may be displayed on a suitable monitor 42 and/or provided to a hard copy printer/plotter (not shown).

Figure 2:
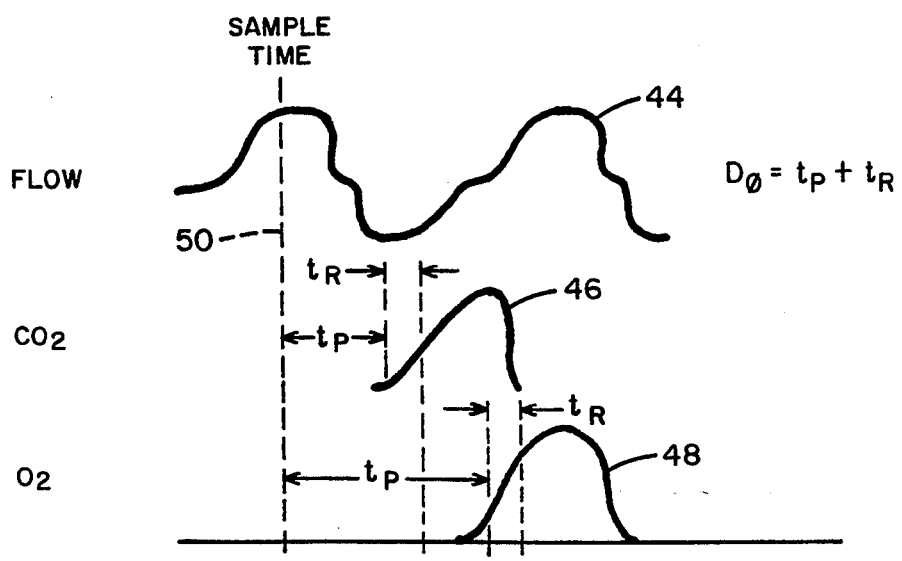
FIG. 2 illustrates by means of a series of waveforms the underlying principles of the present invention.

Referring next to FIG. 2, waveform 44 is a plot of flow vs. time, the flow having been measured using the pneumotach mouthpiece 10 and its associated differential pressure sensor 20. Waveform 46 represents an output from the carbon dioxide sensor 30 while waveform 48 represents an output from the oxygen sensor 32. The sampling time is indicated by the vertical dashed line 50 and a measurable delay $t_p$ occurs before either the $CO_2$ sensor 30 or the $O_2$ sensor 32 begins to respond. The end of the transit time may arbitrarily defined as the point at which the output from the sensors 30 or 32 reach, say, two percent of their maximum output. Following that, there is a fixed delay interval, $t_R$, corresponding to the response time of the sensor itself. The response time may arbitrarily be defined as the time required for the sensor to reach 50 percent of its maximum output.

While $t_R$ is a fixed known value, $t_p$, i.e., the transit time, varies as a function of the sample flow rate.

To properly align the phase of the outputs from the individual gas sensors 30 and 32 with a corresponding flow measurement, at the time that the cardiopulmonary performance analyzer is initially calibrated, the gas transit time, $t_c$, through the sample line is measured for a known flow rate, $F_c$. The values of transit time and sample flow rate at the time of calibration are stored in the memory of the microprocessor. Subsequently, during the course of a cardiopulmonary performance test on a patient, the sample flow sensor 34 is used to measure the sample flow rate. The microprocessor 24 is programmed to calculate the gas transit time, $t_c$, in the sample line to each of the plurality of gas sensors in accordance with the formula:

$$t_p = t_c(F_c/F_s)$$

By adding the thus calculated current gas transit time, $t_p$, to the known, fixed response time of the gas sensor, the phase delay between the expiratory flow and the gas concentration measurements is obtained. Knowing the total phase delay allows the computer to time-wise align gas concentration readings with the flow signal. By measuring flow in the sample line and using the measured value calculate the associated current transit time, flow is dynamically aligned with the gas concentration waveforms and changing sample line flow rates are compensated for.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. For use in microprocessor-based cardiopulmonary performance analyzing system of the type including a flow meter for measuring inspiratory and expiratory flow and a gas sample line having a plurality of gas sensors therealong for measuring the concentration of respiratory gases in an expired sample volume of such respiratory gases, said gas sensors having a known, fixed response time, a method for time-wise aligning the concentration measurements of the respiratory gases with the flow measurements of said expired sample comprising the steps of:

(a) sensing at a predetermined calibration time the gas transit time through said sample line for a known flow rate and producing first signals proportional thereto;

(b) digitizing and storing said first signals in a memory of a microprocessor;

(c) measuring a sample flow during the course of a cardiopulmonary test on a patient and producing a second digitized signal proportional thereto;

(d) calculating from said stored first signal and said second digitized signal the present gas transit time in said sample line to each of said plurality of gas sensors (d) (e) adding the calculated present gas transit time to said known, fixed response time of said gas sensors to obtain the phase delay between the expiratory flow and said concentration measurement.

2. In a cardiopulmonary performance analyzer of the type having a sample line leading to at least one respiratory gas analyzer, said gas analyzer adapted to measure the percentage concentration of a particular gas present in the sample line, means for drawing a sample of respiratory gas through said sample line, and a flow meter for measuring the volume rate of flow of inspired and expired respiratory gases by a patient, the improvement comprise apparatus for compensating for transit time delays between the time a gas sample is drawn into said sample line and the time that said at least one gas analyzer produces a predetermined output response comprising:

(a) microprocessor means operative at an initial calibration time for computing and storing digital values proportional to the transit time of an initial gas sample drawn into said sample line to reach said at least one gas analyzer and for storing a calibration flow rate for said initial gas sample;

(b) sample flow measuring means in said sample line for producing a signal proportional to a rate of flow of a subsequent gas sample later drawn through said sample line during the course of a cardiopulmonary test on a patient;

(c) means for digitizing said signal proportional to the rate of flow of the subsequent gas sample;

(d) computing means including said microprocessor means for receiving said digitized signal and the stored values for said transit time and sample flow rate of said initial gas sample stored at the calibration time for computing a present gas transit time;

(e) means in said microprocessor means responsive to the computed transit time value for time-wise aligning said measured percentage concentration of said particular gas with said measured volume rate of flow of inspired and expired respiratory gases.

* * * * *

UNITED STATES PATENT AND TRADEMARK OFFICE
CERTIFICATE OF CORRECTION

PATENT NO. : 5,398,695
DATED : March 21, 1995
INVENTOR(S) : David M. Anderson and Shawn McCutcheon It is certified that error appears in the above-indentified patent and that said Letters Patent is hereby corrected as shown below:

Column 4, line 67, delete "(d)".

Column 6, line 12, after "stored" insert -- digital --.

Signed and Sealed this

Thirteenth Day of June, 1995

*Attest:*

BRUCE LEHMAN

*Attesting Officer*     *Commissioner of Patents and Trademarks*